United States Patent [19]

Frater et al.

[11] Patent Number: 4,556,413
[45] Date of Patent: Dec. 3, 1985

[54] CERTAIN ARYLOXY-BENZOYL SULFOXIMINES HAVING HERBICIDAL ACTIVITY

[75] Inventors: Georg Frater, Greifensee; Milos Suchy, Pfaffhausen; Jean Wenger, Uster; Paul Winternitz, Greifensee, all of Switzerland

[73] Assignee: Hoffmann-La Roche Inc., Nutley, N.J.

[21] Appl. No.: 546,243

[22] Filed: Oct. 28, 1983

[30] Foreign Application Priority Data

Nov. 4, 1982 [CH] Switzerland ............ 6418/82
Sep. 6, 1983 [CH] Switzerland ............ 4873/83

[51] Int. Cl.⁴ ............ C07D 213/64; C07C 145/02; A01N 43/40; A01N 41/02
[52] U.S. Cl. ............ 71/94; 71/103; 546/300; 564/101
[58] Field of Search ............ 546/300; 564/101; 71/94, 103

[56] References Cited

U.S. PATENT DOCUMENTS 4,308,053 12/1981 Cartwright et al. ............ 71/94
4,401,460 8/1983 Cartwright et al. ............ 71/94

*Primary Examiner*—Alan L. Rotman
*Attorney, Agent, or Firm*—Jon S. Saxe; George M. Gould; John J. Maitner

[57] ABSTRACT

Benzoic acid compounds of the formula

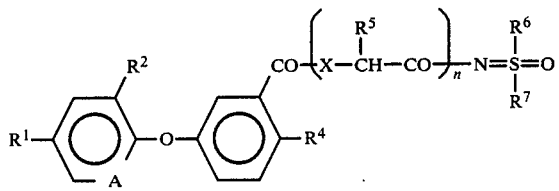

wherein A, $R^1$, $R^2$, $R^4$, $R^5$, $R^6$, $R^7$, n and X are as defined hereinafter, processes for their preparation, herbicidal compositions containing these compounds and methods for the use of the compounds and the herbicidal compositions are disclosed. Novel compounds which useful as starting materials for the preparation of the benzoic acid compounds of formula I are also disclosed.

21 Claims, No Drawings

CERTAIN ARYLOXY-BENZOYL SULFOXIMINES HAVING HERBICIDAL ACTIVITY

SUMMARY OF THE INVENTION

The invention is directed to benzoic acid derivatives of the formula

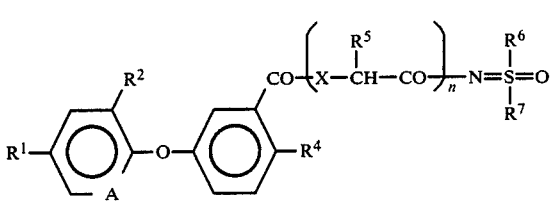

wherein A, $R^1$, $R^2$, $R^4$, $R^5$, $R^6$, $R^7$, n and X are as defined hereinafter, and processes for their preparation. This invention is also directed to herbicidal compositions containing, as the active ingredient, a compound of formula I and methods for the use of these herbicidal compositions. The invention is also directed to novel compounds used as starting materials in the preparation of compounds of formula I.

DETAILED DESCRIPTION OF THE INVENTION

The invention relates to benzoic acid derivatives of the formula

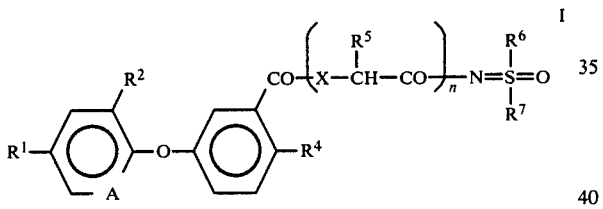

wherein A is N or $CR^3$,
$R^1$ is halogen or trifluoro-methyl,
$R^2$ and $R^3$ independently of one another are hydrogen or halogen,
$R^4$ is halogen, nitro or cyano,
$R^5$ is hydrogen or methyl,
$R^6$ is $C_{1-6}$-alkyl and
$R^7$ is $C_{1-6}$-alkyl, aryl, or aryl substituted with halogen, $C_{1-4}$-alkyl, $C_{1-4}$-alkoxy and/or nitro, or
$R^6$ and $R^7$ together are tetramethylene, pentamethylene or hexamethylene,
n is 0 or 1,
X is oxygen or —$NR^8$—
and $R^8$ is hydrogen or $C_{1-6}$-alkyl.

The invention is also directed to herbicidal compositions which contain, as the active ingredient, a compound of formula I, and methods for their use. The compounds have both preemergence and postemergence herbicidal activity.

In formula I above the term "halogen" encompasses fluorine, chlorine, bromine or iodine, with chlorine being preferred.

The terms "$C_{1-6}$-alkyl" and "$C_{1-4}$-alkyl" encompass both straight-chain and branched-chain alkyl groups such as methyl, ethyl, n-propyl, isopropyl, n-butyl, neopentyl and n-hexyl. This also applies to a $C_{1-4}$-alkoxy group containing a $C_{1-4}$-alkyl group.

The term "aryl" encompasses a radical derived from an aromatic hydrocarbon. Aryl and substituted aryl are preferably phenyl and substituted phenyl. When two or more substituents are present on the aryl group, these substituents can be the same or different.

Preferred compounds of formula I are those in which independently of one another $R^1$ is trifluoromethyl, $R^2$ is chlorine and $R^3$ which may be present in hydrogen. Most preferably $R^1$ is trifluoromethyl, $R^2$ is chlorine and $R^3$ is hydrogen, all simultaneously.

$R^4$ is preferably nitro.

The preferred alkyl groups denoted by $R^6$ and $R^7$ are those containing 1–3 carbon atoms, preferably methyl.

A particularly preferred compound of formula I is N-[5-(o-chloro-p-trifluoromethyl-phenoxy)-2-nitrobenzoyl]-S,S-dimethyl-sulphoximine.

The compounds of formula I are prepared by one of the procedures described below:

A. Reacting an acid of the formula

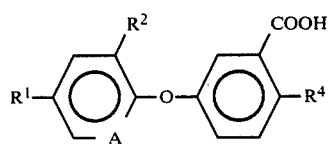

wherein A, $R^1$, $R^2$ and $R^4$ are as described previously, in the form of a reactive derivative with a sulphoximine of the formula

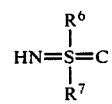

wherein $R^6$ and $R^7$ are as described previously, or with an alkali metal salt thereof.

This procedure leads to those compounds of formula I wherein n is 0. This procedure can be carried employing procedures well known to those skilled in the art. The following embodiments can be used depending on the nature of the reactants:

Variant ($a_1$): A reactive derivative of an acid of formula II such as the corresponding O-acyl-1,3-dicyclohexylisourea, the corresponding N-acylimidazole or acid anhydride or a mixed acid anhydride, for example, the acid anhydride formed from the acid of formula II and ethyl chloroformate, is reacted with a sulphoximine of formula III.

Variant ($a_2$): A reactive derivative of an acid of formula II, preferably an acid halide, for example, the acid chloride, is reacted with a sulphoximine of formula III in the presence or an organic base such as tertiary amine, for example triethylamine, dimethylaniline or pyridine, 1,5-diaza-bicyclo[4,3,0]non-5-ene, 1,8-diazabicyclo[4,5,0]undec-7-ene or 1,4-diaza-bicyclo[2,2,2]octane.

Variant ($a_3$): A reactive derivative of an acid of formula II, preferably an acid halide, for example, the acid chloride, is reacted with an alkali metal salt of a sulphoximine of formula III such as the lithium, sodium or preferably, potassium salt.

In certain cases the reactive derivative of the acid of formula II is conveniently prepared in situ and is reacted without isolation with the sulphoximine of formula III in the same reaction medium. Thus, for example, an acid of formula II is reacted with dicyclohexylcarbodiimide to give the corresponding O-acyl-1,3-dicyclohexylisourea or acid anhydride and the urea or the anhydride is subsequently reacted with the sulphoximine in the same reaction medium.

The reaction in accordance with this procedure is conveniently carried out in an inert organic diluent such as an aliphatic or cyclic ether, for example, diethyl ether, tetrahydrofuran or dioxan, a hydrocarbon, for example, toluene, or a halogenated hydrocarbon, for example, methylene chloride. It is conveniently carried out at a temperature between −20° C. and 100° C., preferably between 0° and 70° C.

B. Reacting a salt or a reactive derivative of an acid of formula II given above with a compound of the formula

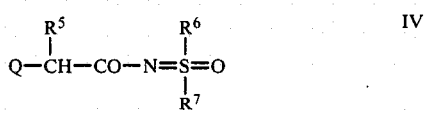

wherein $R^5$, $R^6$ and $R^7$ are as described previously, and Q is a leaving group or hydroxy.

This procedure leads to those compounds of formula I wherein n is 1 and X is oxygen. This process procedure is an esterification which can be carried out according to methods known to those skilled in the art. Thus, for example, a salt of an acid of formula II is reacted with a compound of formula IV in which Q is a leaving group, preferably chlorine, bromine, iodine, mesyloxy or tosyloxy. The reaction is conveniently carried out in an inert diluent and at temperatures of about −20° C. to 150° C., preferably in the temperature range of 0° C. to 100° C. The salts of the acid of formula II are suitably alkali metal salts, for example, the sodium, potassium or lithium salt, alkaline earth metal salts, for example, the magnesium, calcium or barium salt, salts with organic bases such as trialkylamines, for example, triethylamine, 1,5-diaza-bicyclo-[4,3,0]non-5-ene, 1,8-diaza-bicyclo[4,5,0]undec-7-ene and 1,4-diaza-bicyclo[2,2,2]octane, whereby the alkali metal salts are preferred. The diluents which can be used are preferably inert organic solvents such as aliphatic and cyclic ethers, for example, diethyl ether, tetrahydrofuran and dioxan, aromatics, for example, benzene and toluene, and dimethylformamide, dimethyl sulphoxide and hexamethylphosphoric acid triamide.

The salt of the acid of formula II is conveniently prepared in situ by reacting the acid with a suitable inorganic base, for example, an alkali metal or alkaline earth metal carbonate or bicarbonate, or an organic base, to give the salt which is subsequently reacted in the same reaction medium with the compound of formula IV.

When a reactive derivative of the acid of formula II is used, Q in formula IV is hydroxy. The reactive derivative of the acid of formula II is preferably an acid halide, particularly, the acid chloride, however, it can also be, for example, the corresponding O-acyl-1,3-dicyclohexyl-isourea or the corresponding N-acylimidazole or acid anhydride.

In certain cases the reactive derivative of the acid of formula II is conveniently prepared in situ and this is reacted in the same reaction medium without isolation with the compound of formula IV. Thus, for example, an acid of formula II is reacted with dicyclohexylcarbodiimide to give the corresponding O-acyl-1,3-dicyclohexylisourea or acid anhydride and this is subsequently reacted with the compond of formula IV in the same reaction medium.

The reaction is conveniently carried out in an inert solvent such as an aliphatic or cyclic ether, for example, diethyl ether, tetrahydrofuran or dioxan, an aliphatic or aromatic hydrocarbon, for example, n-hexane, benzene or toluene, or a halogenated, preferably chlorinated, hydrocarbon, for example, methylene chloride or chloroform, and at temperatures from about −20° C. to 150° C., preferably from 0° C. to 50° C.

When an acid halide of the acid of formula II is used, the reaction is conveniently carried out in the presence of an acid-binding agent. Inorganic bases, for example, alkali metal and alkaline earth metal carbonates and bicarbonates, and organic bases, for example, tertiary amines, preferably triethylamine and pyridine, 1,5-diaza-bicyclo[4,3,0]-non-5-ene, 1,8-diaza-bicyclo[4,5,0]undec-7-ene and 1,4-diaza-bicyclo[2,2,2]octane have been found to be suitable.

C. Reacting a compound of the formula

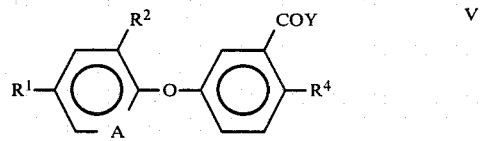

wherein A, $R^1$, $R^2$ and $R^4$ are as described previously, Y is —$NHR^8$ or halogen and $R^8$ is as described previously, with a compound of the formula

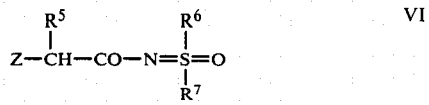

wherein $R^5$, $R^6$ and $R^7$ are as described previously, and Z represents a leaving group such as chlorine, bromine, iodine, mesyloxy or tosyloxy when Y is is —$NHR^8$, and —$NHR^8$ when Y is halogen such as chlorine or bromine.

This procedure leads to those compounds of formula I wherein n is 1 and X is —$NR^8$—.

The reaction of a compound of formula V in which Y is —$NHR^8$ with a compound of formula VI in which Z is a leaving group can be carried out according to methods known per se, the amine of formula V conveniently being present in the form of a salt. Thus the compound of formula V is conveniently reacted in the form of an alkali metal salt (e.g. the lithium, sodium or potassium salt) or in the form of an alkaline earth metal salt (e.g. the calcium, magnesium or barium salt) with a compound of formula VI in which Z is chlorine, bromine, iodine, mesyloxy or tosyloxy. The reaction is conveniently carried out in the presence of an inert diluent and at temperatures from about −20° C. to 150° C., preferably in the temperature range of 0° C. to 100° C. As diluents there can be used especially inert organic solvents such as aliphatic or cyclic ethers, for example, diethyl ether, tetrahydrofuran and dioxan, aromatics, for example, benzene and toluene, dimethylformamide, dimethyl sulfoxide and hexamethylphosphoric acid triamide. The benzamide salt of formula V is preferably a benzamide alkali metal salt and the compound of formula VI is preferably the bromide.

When a compound of formula V in which Y is halogen is reacted with a compound of formula VI in which Z stands for —NHR$^8$, Y is preferably chlorine or bromine, with chlorine being especially preferred. Thus, in this case an acid halide is reacted with an amine to form an amide. The reaction is conveniently carried out in the presence of an inert diluent, especially an organic solvent such as an aliphatic or cyclic ether, for example, diethyl ether, tetrahydrofuran or dioxan, an aromatic, for example benzene or toluene, or a halogenated, preferably chlorinated, hydrocarbon, for example, methylene chloride or chloroform, and in the presence of an organic acid-binding agent such as a tertiary amine, for example triethylamine or pyridine. The reaction is conveniently carried out at temperatures between −20° C. and 100° C., preferably between 0° C. and 20° C.

D. Reacting a phenol of the formula

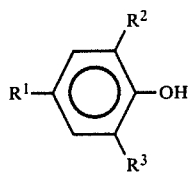
VII wherein R$^1$, R$^2$ and R$^3$ are as described previously, or an alkali metal salt thereof with a halide of the formula

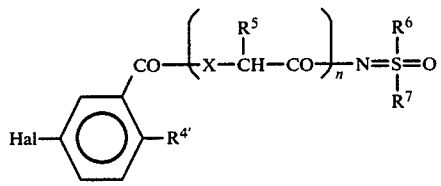
VIII wherein R$^5$, R$^6$, R$^7$, n and X are as described previously, R$^{4'}$ is nitro or cyano and Hal is halogen, preferably fluorine.

E. Reacting a hydroxybenzoic acid derivative of the formula

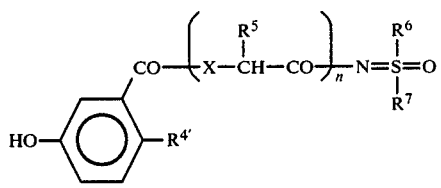
IX wherein R$^4$, R$^5$, R$^6$, R$^7$, n and X are as described previously, or an alkali metal salt thereof with a halide of the formula

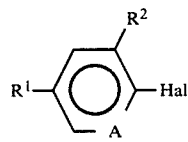
X wherein A, R$^1$ and R$^2$ are as described previously, and Hal is halogen, with the proviso that R$^1$ is trifluoromethyl when A is CR$^3$ and R$^2$ and/or R$^3$ is halogen.

Procedures D and E lead to those compounds of formula I in which A is CR$^3$ and R$^4$ is nitro or cyano, or A is N or CR$^3$, with the proviso that in the case of procedure E R$^1$ is trifluoromethyl when A is CR$^3$ and R$^2$ and/or R$^3$ represents halogen. The symbol "Hal" in formulae VIII and X encompasses fluorine, chlorine, bromine and iodine. The reaction can be carried out conveniently by converting the phenol of formula VII or the hydroxybenzoic acid derivative of formula IX into an alkali metal salt, for example using sodium hydride or potassium hydroxide with azeotropic removal of water, and subsequently reacting the salt with the halide of formula VIII or X. The latter reaction step is conveniently carried out in a dipolar aprotic solvent, for example dimethylformamide or dimethyl sulfoxide, or in pyridine at temperatures between 50° C. and 200° C., preferably between 100° C. and 180° C.

F. Nitrating a compound of the formula

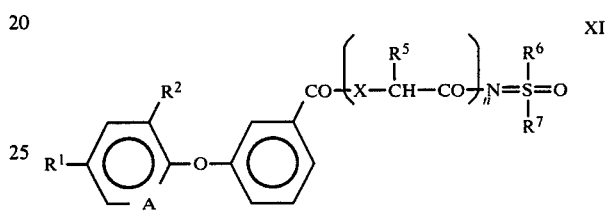
XI wherein A, R$^1$, R$^2$, R$^5$, R$^6$, R$^7$, n and X are as described previously.

The nitration procedure leads to those compounds of formula I in which R$^4$ is nitro. The reaction is conveniently carried out using nitric acid or mixtures or solutions containing nitric acid such as mixtures of nitric acid and sulfuric acid, solutions of nitric acid in glacial acetic acid and solutions of concentrated nitric acid in chlorinated hydrocarbons, for example methylene chloride. Nitration can also be carried out using nitronium tetrafluoroborate, nitronium hexafluorophosphate or acetyl nitrate. The nitration reaction is conveniently carried out at temperatures between 0° C. and 200° C., preferably between 0° C. and 25° C.

Isolation and purification of the compounds of formula I can be carried out using conventional techniques.

The starting materials for formulae II to X as well as the salts and the reactive derivatives of the acids of formula II and the alkali metal salts of the compounds of formulae III, VII and IX are in part known. The novel N-(5-fluoro-2-nitrobenzoyl)-S,S-dimethyl-sulphoximine (VIII') and the novel N-(5-hydroxy-2-nitrobenzoyl)-S,S,-dimethyl-sulphoximine (IX' ) form a further object of the present invention. These compounds can be prepared according to procedures known to one skilled in the art.

The compounds of formula XI used as starting materials in procedure F are novel compounds which form a further object of the present invention. These compounds, for example N-[3-(o-chloro-p-trifluoromethylphenoxy)-benzoyl]-S,S-dimethyl-sulphoximine, can be prepared according to methods which are analogous to procedures A–E set forth above. The following Reaction Schemes indicate the routes to the compounds of formula XI.

Reaction Schemes:
Preparation of the compounds of general formula XI (a') 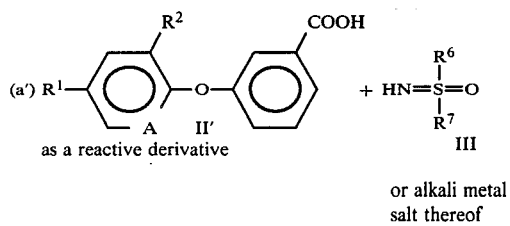

or alkali metal salt thereof

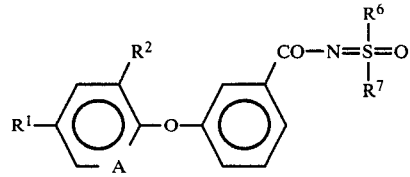

(b') 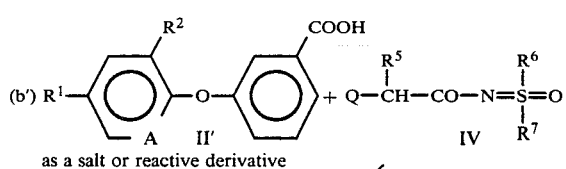
as a salt or reactive derivative

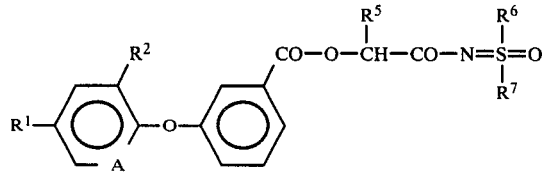

(c') 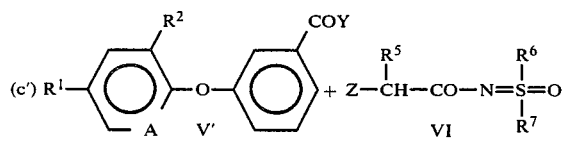

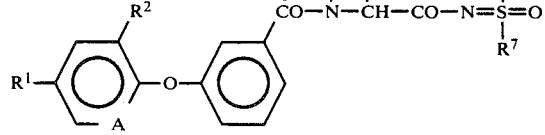

(d') 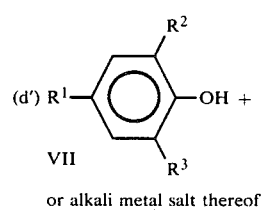

or alkali metal salt thereof

-continued
Reaction Schemes:
Preparation of the compounds of general formula XI

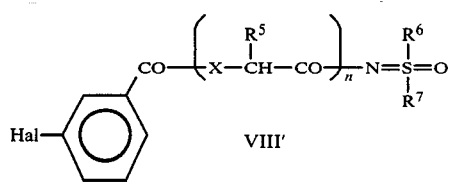

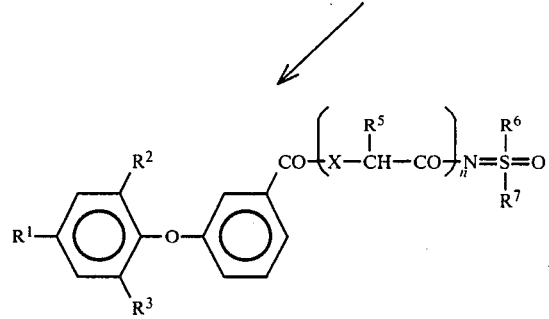

(e') 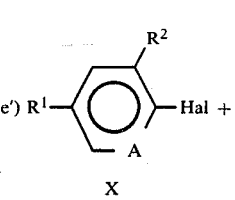

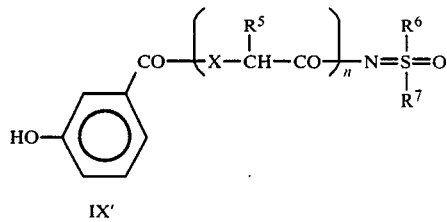

or alkali metal salt thereof

In the above Reaction Schemes A, $R^1$–$R^8$, n, X, Q, Y, Z and Hal are as described previously. The reactions in accordance with variants (a')–(e') are conveniently carried out under those reaction conditions which are given above in connection with the corresponding procedures A–E. The compounds of formulae II', V', VIII' and IX' used as starting materials as well as salts and reactive derivatives of the acids of formula II' and alkali metal salts of the compounds of formula IX' are either known or can be prepared according to conventional procedures known to one skilled in the art.

Where asymmetric carbon atoms are present in the molecule, the compounds of formula I occur in optically active isomeric forms. When a chiral sulfur atom is present in the compounds of formula I, i.e. when $R^6$ and $R^7$ are different, optical isomerism occurs. Formula I is accordingly intended to include the racemates as well as all of these possible isomeric forms.

Where asymmetric carbon atoms are present in the molecule of formula I and no planned synthesis for the isolation of pure optical isomers is carried out, the product normally occurs as the racemate. The isomers can be separated according to methods known per se. If desired, the optical isomers can, of course, also be manufactured by synthesis from corresponding optically active starting materials.

The compounds of formula I are useful as both pre-emergent and post-emergent herbicides. They are particularly suitable in combatting weeds such as *Galium aparine, Amaranthus retroflexus, Datura stramonium, Ipomea* spp., *Abutilon theophrasti, Chenopodium album, Sorghum bicolor, Daucus carota* and *Cassia obtusifolia* in cereals, especially in barley, oats, wheat, rice, peanut and soya crops. The compunds of formula I are particularly useful for the control of weeds in wheat, rice, peanut and soya crops. Use as post-emergent herbicides is preferred.

In general, the compounds of formula I are effective as herbicides when applied at a concentration of about 0.05 to about 2 kg/ha with the preferred concentration range being from about 0.1 to about 1 kg/ha.

This invention is also directed to herbicidal compositions which comprise inert carrier material and, as the active ingredient, one or more compounds of formula I. These herbicidal compositions suitably contain, as the inert carrier material, at least one of the following ingredients: solid carrier materials, solvents or dispersion media, tensides (wetting and emulsifying agents), dispersing agents (without tenside action) and stabilizers. The herbicidal compositions of this invention can be formulated in the usual forms, for example dusts, powders, granulates, solutions, emulsions, suspensions, emulsifiable concentrates, pastes, and the like.

The compounds of formula I are in general water-insoluble. Thus, the usual methods of formulation of insoluble materials can be employed. For example, the compounds can be mixed with solid carrier substances, dissolved or suspended in suitable solvents or dispersion media, if necessary using tensides as wetting or emulsifying agents and/or dispersing agents, diluting pre-prepared emulsifiable concentrates with solvents or dispersion media, etc.

Suitable solid carrier materials include natural mineral substances, such as chalk, dolomite, limestone, aluminas, and silicic acid and salts thereof, for example, siliceous earth, kaolin, bentonite, talc, attapulgite and montmorillonite; synthetic mineral substances, such as highly dispersible silicic acid, aluminium oxide and silicates; organic substances, such as cellulose, starch, urea and synthetic resins; and fertilizers, such as phosphates and nitrates. The solid carrier substances can be present, for example, as powders or as granulates.

Suitable solvents or dispersion media include aromatic hydrocarbons, such as benzene, toluene, xylenes and alkylnaphthalenes; chlorinated aromatic and chlorinated aliphatic hydrocarbons, such as chlorobenzenes, chloroethylenes and methylene chloride; aliphatic hydrocarbons, such as cyclohexane and paraffins, for example, petroleum fractins; alcohols, such as butanol and glycol, as well as their ethers and esters; ketones, such as acetone, methyl ethyl ketone, methyl isobutyl ketone and cyclohexanone; and strongly polar solvents or dispersion media such as dimethylformamide, N-methylpyrrolidone and dimethyl sulfoxide, whereby such solvents or dispersion media preferably have flash points of at least 30° C. and boiling points of at least 50° C., and water. Also included in the solvents or dispersion media which can be used in preparing the herbicidal compositions are the so-called liquified gaseous extenders or carrier substances, these being products which are gaseous at room temperature and under normal pressure. Examples of such products are aerosol propellant gases such as halogenated hydrocarbons, for example, dichlorodifluoromethane. If a weed control composition in accordance with the invention is present in the form of a pressurized pack, then a solvent is conveniently used in addition to the propellant gas.

Tensides (wetting and emulsifying agents) suitable for use with the compounds of this invention can be anionic, cationic or nonionic.

Examples of anionic tensides include soaps; fatty sulfate esters, such as dodecyl sodium sulfate, octadecyl sodium sulfate and cetyl sodium sulfate; alkyl sulfonates, aryl sulfonates and fatty-aromatic sulfonates, such as alkylbenzenesulfonates, for example, calcium dodecylbenzene sulfonate, and butylnaphthalene-sulfonates; and the more complex fatty sulfonates, such as the amide condensation products of oleic acid and N-methyltaurine or the sodium sulfonate of dioctyl succinate.

Examples of nonionic tensides include, for example, condensation products of fatty acids, fatty alcohols or fatty-substituted phenols with ethylene oxide; fatty acid esters and ethers of sugars or polyhydric alcohols; condensation products of sugars or polyhydric alcohols with ethylene oxide; block copolymers of ethylene oxide and propylene oxide, or alkyldimethylamine oxides.

Examples of cationic tensides include alkyldimethylbenzylammonium chlorides, dialkyldimethylammonium chlorides, alkyltrimethylammonium chlorides and ethoxylated quaternary ammonium chlorides.

Suitable dispersing agents (without tenside action) include lignin, sodium and ammonium salts of lignin sulphonic acids, sodium salts of maleic acid anhydride/diisobutylene copolymers, sodium and ammonium salts of sulphonated polycondensation products of naphthalene and formaldehyde, and sulphite lyes.

Dispersing agents which are especially suitable as thickening agents or antisettling agents include methylcellulose, carboxymethylcellulose, hydroxyethylcellulose, polyvinyl alcohol, alginates, caseinates and blood albumin.

Examples of suitable stabilizers are acid-binding agents, for example, epichlorohydrin, phenyl glycidyl ether, soya epoxides and the like; antioxidants, for example, gallic acid esters, butylhydroxytoluene and the like; UV-absorbers, for example, substituted benzophenones, diphenylacrylonitrile acid esters, cinnamic acid esters and the like; and deactivators, for example, salts of ethylenediaminotetraacetic acid, polyglycols and the like.

The herbicidal compositions of this invention can also contain, in addition to the compounds of formula I, synergistic agents and other active ingredients, such as insecticides, acaricides, bactericides, other herbicides, fungicides, plant growth regulators and fertilizers. Such combination preparations are suitable for increasing the activity or for broadening the spectrum of activity.

The herbicidal compositions of this invention generally contain between 0.005 and 95 percent by weight, preferably between 5 and 80 percent by weight, of one or more compounds of formula I as the active ingredient. The composition can be in the form of emulsifiable concentrates suitable for storage and shipment. In such concentrate formulations the active substance concentration is normally in the higher range, preferably between 10 and 80 percent by weight, especially between 25 and 75 percent by weight. These formulations can subsequently be diluted, for example, with the same or different inert ingredients, to give active ingredient concentrations which are suitable for practical use, i.e. preferably about 0.005 to 2 percent by weight, especially about 0.05 to 1 percent by weight. The active ingredient concentrations can, however, also be smaller or greater.

The herbicidal compositions of this invention can be prepared according to known formulation procedures.

For the preparation of pulverous preparations, the active ingredient, i.e. at least one compound of formula I, can be mixed with solid carrier materials, for example, by grinding the ingredients together, or the solid carrier material can be impregnated with a solution or suspension of the active ingredient and then the solvent or dispersion medium can be removed by evaporation, heating, or by vacuum under reduced pressure. By adding tensides or dispersing agents, such pulverous preparations can be made readily wettable with water, so that they can be converted into aqueous suspensions which are suitable, for example, as spray compositions.

The compounds of formula I can also be mixed with a tenside and a solid carrier material to form a wettable powder which is dispersible in water, or they can be mixed with a solid pregranulated carrier material to form a granulate.

If desired, the compounds of formula I can be dissolved in a water-immiscible solvent, such as, for example, a high-boiling hydrocarbon, which conveniently contains a dissolved emulsifying agent, so that the solution becomes self-emulsifying upon addition to water. Alternatively, the active ingredient can be mixed with an emulsifying agent, and the mixture can then be diluted with water to the desired concentration. Moreover, the active ingredient can be dissolved in a solvent, and thereafter the solution can be mixed with an emulsifying agent. Such a mixture can likewise be diluted with water to the desired concentration. In this manner there are obtained emulsifiable concentrates or ready-for-use emulsions.

The use of the herbicidal compositions of this invention can be carried out according to usual application methods, such as sprinkling, spraying, dusting, pouring or scattering. The method of this invention for the control of weeds comprises treating the locus to be protected against weeds and/or the weeds with a compound of formula I or with a herbicidal composition in accordance with the invention.

The following Examples illustrate the present invention:

I. Preparation of the compounds of formula I

EXAMPLE 1

A solution of 20.63 g of dicyclohexylcarbodiimide in 100 ml of methylene chloride is added dropwise at 5°–10° C. while stirring during 10 minutes to a solution of 36.14 g of 5-(o-chloro-p-trifluoromethyl-phenoxy)-2-nitro-benzoic acid in 1.5 l of methylene chloride. A solution of 9.31 g of dimethyl sulphoximine in 50 ml of methylene chloride is subsequently added dropwise to the suspension at 20° C. during 5 minutes and the mixture is stirred at room temperature for 20 hours. The insoluble dicyclohexylurea formed is filtered off under suction and the filtrate is evaporated under reduced pressure. The residue is purified by chromatography on silica gel with diethyl ether.

There is obtained N-[5-(o-chloro-p-trifluoromethyl-phenoxy)-2-nitrobenzoyl]-S,S-dimethyl-sulphoximine as colourless crystals, m.p. 126°–127° C.; $^1$H-NMR (CDCl$_3$): 7.99 (d,1H), 7.80 (d,1H), 7.60 (q,1H), 7.23 (d,1H), 7.14 (d,1H), 7.02 (q,1H) and 3.40 (s,6H).

In an analogous manner, from 5-(o-chloro-p-trifluoromethyl-phenoxy)-2-nitro-benzoic acid and ethyl methyl sulphoximine there is obtained N-[5-(o-chloro-p-trifluoromethyl-phenoxy)-2-nitrobenzoyl]-S-ethyl-S-methyl-sulphoximine as a colourless viscous oil; $^1$H-NMR (CDCl$_3$): 7.96 (d,1H), 7.80 (d,1H), 7.59 (q,1H), 7.22 (d,1H), 7.16 (d,1H), 7.01 (q,1H), 3.48 (m,2H), 3.37 (s,3H) and 1.5 (t,3H);

from 5-(o-chloro-p-trifluoromethyl-phenoxy)-2-nitro-benzoic acid and diethyl sulphoximine there is obtained N-[5-(o-chloro-p-trifluoromethyl-phenoxy)-2-nitrobenzoyl]-S,S-diethyl-sulphoximine as a pale yellow viscous resin; $^1$H-NMR (CDCl$_3$): 7.92 (d,1H), 7.80 (d,1H), 7.58 (q,1H), 7.21 (d,1H), 7.20 (d,1H), 7.00 (q,1H), 3.52 (m,4H) and 1.49 (t,6H);

from 5-(o-chloro-p-trifluoromethyl-phenoxy)-2-nitro-benzoic acid and methyl phenyl sulphoximine there is obtained N-[5-(o-chloro-p-trifluoromethyl-phenoxy)-2-nitrobenzoyl]-S-methyl-S-phenyl-sulphoximine as a pale yellow viscous resin; $^1$H-NMR (CDCl$_3$): 8.02 (m,2H), 7.97 (d,1H), 7.79 (d,1H), 7.71 (m,1H), 7.63 (m,2H), 7.58 (q,1H), 7.21 (d,1H), 7.19 (d,1H), 7.04 (q,1H) and 3.53 (s,3H);

from 5-(o-chloro-p-trifluoromethyl-phenoxy)-2-nitro-benzoic acid and (n-hexyl)methyl sulphoximine there is obtained N-[5-(o-chloro-p-trifluoromethyl-phenoxy)-2-nitrobenzoyl]-S-(n-hexyl)-S-methyl-sulphoximine as a yellow viscous resin; $^1$H-NMR (CDCl$_3$): 8.1–6.9 (m,6H), 3.7–3.3 (m,5H) and 2.2–0.8 (m,11H);

from 5-(o-chloro-p-trifluoromethyl-phenoxy)-2-nitro-benzoic acid and methyl(p-chlorophenyl)sulphoximine there is obtained N-[5-(o-chloro-p-trifluoromethyl-phenoxy)-2-nitrobenzoyl]-S-methyl-S-(p-chlorophenyl)-sulphoximine as a pale yellow resin; $^1$H-NMR (CDCl$_3$): 7.99–7.92 (m,3H), 7.79 (d,1H), 7.65–7.55 (m,3H), 7.22 (d,1H), 7.18 (d,1H), 7.05 (q,1H), 3.50 (s,3H);

from 5-(o-chloro-p-trifluoromethyl-phenoxy)-2-nitro-benzoic acid and methyl(p-tolyl)sulphoximine there is obtained N-[5-(o-chloro-p-trifluoromethyl-phenoxy)-2-nitrobenzoyl]-S-methyl-S-(p-tolyl)-sulphoximine as a yellow resin; $^1$H-NMR (CDCl$_3$): 7.95 (d,1H), 7.89 (m,2H), 7.79 (d,1H), 7.58 (q,1H), 7.47 (m,2H), 7.22 (d,1H), 7.19 (d,1H) 7.05 (q,1H), 3.50 (s,3H), 2.47 (s,3H);

from 5-(o-chloro-p-trifluoromethyl-phenoxy)-2-nitro-benzoic acid and methyl(o-chlorophenyl)sulphoximine there is obtained N-[5-(o-chloro-p-trifluoromethyl-phenoxy)-2-nitrobenzoyl]-S-methyl-S-(o-chlorophenyl)-sulphoximine as a pale resin; $^1$H-NMR (CDCl$_3$): 8.28 (q,1H), 7.95 (d,1H), 7.79 (d,1H), 7.68–7.52 (m,4H), 7.22 (d,1H), 7.20 (d,1H), 7.02 (q,1H), 3.68 (s,3H);

from 5-(5-trifluoromethyl-2-pyridyloxy)-2-nitro-benzoic acid and dimethyl sulphoximine there is obtained N-[5-(5-trifluoromethyl-2-pyridyloxy)-2-nitrobenzoyl]-S,S-dimethyl-sulphoximine as a yellow resin; $^1$H-NMR (CDCl$_3$): 8.45 (d,1H), 8.02–7.94 (m,2H), 7.50 (d,1H), 7.32 (q,1H), 7.13 (d,1H), 3.40 (s,6H);

from 5-(3,5-dichloro-2-pyridyloxy)-2-nitro-benzoic acid and dimethyl sulphoximine there is obtained N-[5-(3,5-dichloro-2-pyridyloxy)-2-nitrobenzoyl]-S,S-dimethyl-sulphoximine as a yellow resin; $^1$H-NMR (CDCl$_3$): 8.02 (d,1H), 7.98 (d,1H), 7.83 (d,1H), 7.47 (d,1H), 7.29 (q,1H), 3.40 (s,6H);

from 5-(3-chloro-5-trifluoromethyl-2-pyridyloxy)-2-nitrobenzoic acid and dimethyl sulphoximine there is obtained N-[5-(3-chloro-5-trifluoromethyl-2-pyridyloxy)-2-nitrobenzoyl]-S,S-dimethyl-sulphoximine as a pale resin; $^1$H-NMR (CDCl$_3$): 8.30 (d,1H), 8.04 (d,1H), 7.99 (d,1H), 7.55 (d,1H), 7.35 (q,1H), 3.40 (s,6H).

EXAMPLE 2

A solution of 2.46 g of 2-chloro-5-(o-chloro-p-trifluoromethyl-phenoxy)-benzoic acid in 20 ml of methylene chloride is added dropwise at room temperature while stirring to a solution of 1.3 g of dicyclohexylcarbodiimide and 0.6 g of dimethyl sulphoximine in 5 ml of methylene chloride, a slight exothermic reaction occurring. After a reaction time of 15 minutes the solvent is removed by evaporation under reduced pressure and the residue is purified by chromatography on silica gel with n-hexane/ethyl acetate (9:1). The white crystalline product is then recrystallized from methylene chloride/n-hexane. There is obtained N-[2-chloro-5-(o-chloro-p-trifluoromethyl-phenoxy)-benzoyl]-S,S-dimethyl-sulphoximine, m.p. 128°–131° C.; mass spectrum: m/e 425/427; $^1$H-NMR (CDCl$_3$): 7.8–6.9 (m,6H), 3.4 (s,6H).

In an analogous manner, from 5-(o-chloro-p-trifluoromethyl-phenoxy)-2-iodobenzoic acid and dimethyl sulphoximine there is obtained N-[5-(o-chloro-p-trifluoromethyl-phenoxy)-2-iodobenzoyl]-S,S-dimethyl-sulphoximine, m.p. 88°–91° C.; mass spectrum: m/e 517/519; $^1$H-NMR (CDCl$_3$): 8.0–6.6 (m,6H), 3.4 (s,6H).

EXAMPLE 3

50.40 g of a 25% solution of potassium tert.pentylate in toluene are added dropwise at 25° C. while stirring during 30 minutes to a solution of 9.31 g of dimethyl sulphoximine in 375 ml of absolute 1,2-dimethoxyethane. The suspension is evaporated to dryness under reduced pressure. There is thus obtained the dimethyl sulphoximine potassium salt starting material.

A solution of 38.01 g of 5-(o-chloro-p-trifluoromethyl-phenoxy)-2-nitrobenzoyl chloride in 125 ml of absolute 1,2-dimethoxyethane is added dropwise at 10°–15° C. while stirring during 30 minutes to a suspension of the dimethyl sulphoximine potassium salt in 250 ml of absolute 1,2-dimethoxyethane. The mixture is stirred at room temperature for 24 hours and subsequently evaporated to dryness under reduced pressure. The resinous residue is dissolved in 1.25 l of diethyl ether, the solution is filtered through Celite and the filtrate is evaporated to dryness. The residue is subsequently purified by chromatography on silica gel with methylene chloride. There is obtained N-[5-(o-chloro-p-trifluoromethyl-phenoxy)-2-nitrobenzoyl]-S,S-dimethyl-sulphoximine as colourless crystals, m.p. 126°–127° C.; $^1$H-NMR (CDCl$_3$): 7.99 (d,1H), 7.80 (d,1H), 7.60 (q,1H), 7.23 (d,1H) 7.14 (d,1H), 7.02 (q,1H) and 3.40 (s,6H).

In an analogous manner from tetramethylene sulphoximine potassium salt and 5-(o-chloro-p-trifluoromethyl-phenoxy)-2-nitrobenzoyl chloride there is obtained N-[5-(o-chloro-p-trifluoromethyl-phenoxy)-2-nitrobenzoyl]-S,S-tetramethylene-sulphoximine as a yellow resin; $^1$H-NMR (CDCl$_3$): 8.00 (d,1H), 7.80 (d,1H), 7.60 (q,1H), 7.24 (d,1H), 7.14 (d,1H), 7.03 (q,1H), 3.77 (m,2H), 3.32 (m,2H), 2.36 (m,4H).

EXAMPLE 4

A solution of 4.5 g of 5-(o-chloro-p-trifluoromethyl-phenoxy)-2-nitro-benzoic acid in 50 ml of thionyl chloride is heated at reflux temperature for 1 hour and thereafter evaporated to dryness. There is thus obtained the crude acid chloride.

A solution of 2.5 g of S-methyl-S-(p-nitrophenyl)-sulphoximine and 0.99 g of pyridine in 15 ml of methylene chloride is added dropwise during 10 minutes to a solution of 4.9 g of the crude acid chloride in 20 ml of methylene chloride, the temperature of the mixture rising from 23° C. to 27° C. After completion of the addition the mixture is stirred at room temperature for 30 minutes. The mixture is subsequently poured into 100 ml of water, acidified to pH 1 with concentrated hydrochloric acid and the aqueous phase is extracted twice with 150 ml of ethyl acetate each time. The combined organic phases are washed twice with 100 ml of sodium chloride solution each time, dried over anhydrous sodium sulphate and evaporated to dryness. The resulting viscous orange oil (8.2 g) is purified by chromatography on silica gel ($\phi$=0.063 mm; 400 g) with ethyl acetate/diethyl ether (1:1). There are obtained 5.0 g (73.5% of the theoretical yield) of N-[5-(o-chloro-p-trifluoromethyl-phenoxy-2-nitrobenzoyl]-S-methyl-S-(p-nitrophenyl)-sulphoximine, m.p. 62°–63° C.; $^1$H-NMR (CDCl$_3$): 8.48 (d,2H), 8.257 (d,2H), 7.965 (d,1H), 7.795 (d,1H), 7.595 (double-d,1H), 7.235 (d,1H), 7.182 (d,1H), 7.055 (double-d,1H), 3.52 (s,3H).

In an analogous manner, from 5-(o-chloro-p-trifluoromethyl-phenoxy)-2-nitro-benzoyl chloride and S-methyl-S-(p-methoxyphenyl)-sulphoximine there is obtained N-[5-(o-chloro-p-trifluoromethyl-phenoxy)-2-nitrobenzoyl]-S-methyl-S-(p-methoxyphenyl)-sulphoximine, m.p. 135°–137° C.; $^1$H-NMR (CDCl$_3$): 7.96 (d,1H), 7.92 (d,2H), 7.79 (d,1H), 7.58 (double-d,1H), 7.21 (d,1H), 7.19 (d,1H), 7.075 (d,2H), 7.035 (double-d,1H), 3.89 (s,3H), 3.50 (s,3H).

EXAMPLE 5

A solution of 1.29 g of ethyl chloroformate in 10 ml of absolute acetone is added dropwise while stirring during 30 minutes at −5° C. to a solution of 3.61 g of 5-(o-chloro-p-trifluoromethyl-phenoxy)-2-nitro-benzoic acid and 1.21 g of triethylamine in 30 ml of absolute acetone. The mixture is stirred at room temperature for 2 hours and then a solution of 1.42 g of S,S-tetramethylene-sulphoximine in 5 ml of absolute acetone is added dropwise during 5 minutes. The mixture is stirred at room temperature for 2 hours, evaporated under reduced pressure, the residue is dissolved in diethyl ether and the solution is washed with water. The organic phase is then dried and evaporated to dryness and the residue is purified by chromatography on silica gel with diethyl ether/n-hexane (3:1).

There is obtained N-[5-(o-chloro-p-trifluoromethyl-phenoxy)-2-nitrobenzoyl]-S,S-tetramethylene-sulphoximine as a yellow resin; $^1$H-NMR (CDCl$_3$): 8.00 (d,1H), 7.80 (d,1H), 7.60 (q,1H), 7.24 (d,1H), 7.14 (d,1H), 7.03 (q,1H), 3.77 (m,2H), 3.32 (m,2H), 2.36 (m,4H).

EXAMPLE 6

A solution of 3.1 g of 2-bromopropionic acid in 20 ml of methylene chloride is treated with a solution of 4.2 g of dicyclohexylcarbodiimide in 10 ml of methylene chloride. A solution of 3.1 g of methyl phenyl sulphoximine in 10 ml of methylene chloride is subsequently added at 10° C. and the mixture is stirred at 20° C. for 5 hours. The insoluble dicyclohexylurea formed is filtered off under suction and the filtrate is evaporated under reduced pressure. There is obtained N-(2-bromopropionyl)-S-methyl-S-phenyl-sulphoximine, m.p. 109°–110° C., which is required for the last step of the manufacturing process (following).

0,25 g of sodium hydride is added to a solution of 3.6 g of 5-(o-chloro-p-trifluoromethyl-phenoxy)-2-nitrobenzoic acid in 10 ml of dimethylformamide and the thus-prepared sodium salt of the acid is treated with a solution of 2.9 g of N-(2-bromopropionyl)-S-methyl-S-phenyl-sulphoximine in 5 ml of dimethylformamide. The mixture is subsequently stirred at 60° C. for 4 hours. The sodium bromide formed is filtered off under suction, the filtrate is evaporated under reduced pressure and the residue is purified by chromatography on silica gel with ethyl acetate. There is thus obtained N-{2-[5-(o-chloro-p-trifluoromethyl-phenoxy)-2-nitrobenzoyloxy]-propionyl}-S-methyl-S-phenyl-sulphoximine as a yellow liquid; $^1$H-NMR (CDCl$_3$): 8.05–7.96 (m,3H), 7.8 (double-d,1H), 7.7–7.55 (m,4H), 7.35 (double-d,1H), 7.2 (double-d,1H), 7.0 (m,1H), 5.41 and 5.35 (in each case d,1H), 3.36 (s,3H), 1.62 and 1.61 (in each case d,3H).

In an analogous manner, from 2-bromopropionic acid, ethyl methyl sulphoximine and 5-(o-chloro-p-trifluoromethyl-phenoxy)-2-nitrobenzoic acid there is obtained N-{2-[5-(o-chloro-p-trifluoromethyl-phenoxy)-2-nitrobenzoyloxy]-propionyl}-S-ethyl-S-methyl-sulphoximine as a yellow liquid; $^1$H-NMR (CDCl$_3$): 8.02 (d,1H), 7.81 (d,1H), 7.61 (double-d,1H), 7.37 (double-d,1H), 7.23 (d,1H), 7.03 (m,1H), 5.29 (double-q,1H), 3.52–3.38 (m,2H), 3.24 and 3.23 (in each case s,3H) and 1.59 (d,3H);

from 2-bromopropionic acid, methyl(p-chlorophenyl)sulphoximine and 5-(o-chloro-p-trifluoromethyl-phenoxy)-2-nitrobenzoic acid there is obtained N-{2-[5-(o-chloro-p-trifluoromethyl-phenoxy)-2-nitrobenzoyloxy]-propionyl}-S-methyl-S-(p-chlorophenyl)-sulphoximine as a yellow resin; $^1$H-NMR (CDCl$_3$): 8.02 and 7.99 (double-d,1H), 7.98–7.89 (m,2H), 7.82 and 7.79 (double-d,1H), 7.63–7.54 (m,3H), 7.37 and 7.34 (double-d,1H), 7.23 and 7.19 (double-d,1H), 7.02 and 6.99 (double-q,1H), 5.37 and 5.31 (double-q,1H), 3.36 and 3.34 (double-s,3H), 1.62 and 1.60 (double-d,3H);

from 2-bromopropionic acid, methyl(p-tolyl)sulphoximine and 5-(o-chloro-p-trifluoromethyl-phenoxy)-2-nitrobenzoic acid there is obtained N-{2-[5-(o-chloro-p-trifluoromethyl-phenoxy)-2-nitrobenzoyloxy]-propionyl}-S-methyl-S-(p-tolyl)-sulphoximine as a yellow resin; $^1$H-NMR (CDCl$_3$): 8.02 and 8.00 (double-d,1H), 7.90–7.82 (m,2H), 7.80 and 7.79 (double-d,1H), 7.60 and 7.57 (double-q,1H), 7.44–7.34 (m,3H), 7.23 and 7.18 (double-d,1H), 7.02 and 6.99 (double-q,1H), 5.40 and 5.35 (double-q,1H), 3.35 and 3.34 (double-s,3H), 2.46 and 2.44 (double-s,1H), 1.63 and 1.61 (double-d,3H);

from 2-bromopropionic acid, S,S-tetramethylene sulphoximine and 5-(o-chloro-p-trifluoromethyl-phenoxy)-2-nitrobenzoic acid there is obtained N-{2-[5-(o-chloro-p-trifluoromethyl-phenoxy)-2-nitrobenzoyloxy]-propionyl}-S,S-tetramethylene-sulphoximine as a yellow resin; $^1$H-NMR(CDCl$_3$): 8.01 (d,1H), 7.81 (d,1H), 7.61 (q,1H), 7.37 (d,1H), 7.24 (d,1H), 7.03 (q,1H), 5.32 (q,1H), 3.65–3.54 (m,2H), 3.32–3.21 (m,2H), 2.40–2.22 (m,4H), 1.60 (d,3H);

from chloroacetic acid, dimethyl sulphoximine and 5-(o-chloro-p-trifluoromethyl-phenoxy)-2-nitrobenzoic acid using 1,5-diaza-bicyclo[5,4,0]undec-5-ene as the base and toluene as the solvent there is obtained N-{[5-(o-chloro-p-trifluoromethyl-phenoxy)-2-nitrobenzoyloxy]acetyl}-S,S-dimethyl-sulphoximine as a yellow resin; $^1$H-NMR (CDCl$_3$): 8.23–6.92 (m, 6H), 4.87 (s,2H), 3.37 (s,6H);

from 2-bromopropionic acid, dimethyl sulphoximine and 5-(o-chloro-p-trifluoromethyl-phenoxy)-2-nitrobenzoic acid using sodium methylate as the base and 1,2-dimethoxyethane as the solvent there is obtained N-{2-[5-(o-chloro-p-trifluoromethyl-phenoxy)-2-nitrobenzoyloxy]-propionyl}-S,S-dimethyl-sulphoximine as a yellow resin; $^1$H-NMR (CDCl$_3$): 8.20–6.90 (m,6H), 5.28 (q,1H), 3.37 (s,6H), 1.62 (d,3H);

from 2-bromopropionic acid, S-methyl-S-(p-methoxyphenyl)-sulphoximine and 5-(o-chloro-p-trifluoromethyl-phenoxy)-2-nitrobenzoic acid there is obtained N-{2-[5-(o-chloro-p-trifluoromethyl-phenoxy)-2-nitrobenzoyloxy]-propionyl}-S-methyl-S-(p-methoxyphenyl)-sulphoximine; m.p. 48°–58° C.; $^1$H-NMR (CDCl$_3$): 8.20 and 7.995 (double-d,2H), 7.92 and 7.89 (double-d,2H), 7.81 and 7.79 (double-d,1H), 7.60 and 7.58 2x double-d,1H), 7.395 and 7.35 (double-d,1H), 7.22 and 7.18 (double-d,1H), 7.06 and 7.03 (double-d,2H), 7.01 and 6.98 (2x double-d,1H), 5.40 and 5.35 (double-q,1H), 3.885 and 3.87 (double-s,3H), 3.35 and 3.336 (double-s,3H), 1.63 and 1.605 (double-d,3H);

from 2-bromopropionic acid, S-methyl-S-(p-nitrophenyl)-sulphoximine and 5-(o-chloro-p-trifluoromethyl-phenoxy)-2-nitrobenzoic acid there is obtained N-{2-[5-(o-chloro-p-trifluoromethyl-phenoxy)-2-nitrobenzoyloxy]-propionyl}-S-methyl-S-(p-nitrophenyl)-sulphoximine; m.p. 58°–64° C.; $^1$H-NMR (CDCl$_3$): 7.95 and 7.925 (double-d,2H), 7.725 and 7.70 (double-d,2H), 7.515 and 7.48 (double-d,1H), 7.315 and 7.285 (double-d,1H), 7.12 and 7.088 (2x double-d,1H), 6.885 and 6.80 (double-d,1H), 6.75 and 6.697 (double-d,1H), 6.535 and 6.48 (2x double-d,1H), 5.35 and 5.250 (double-q,1H), 4.01 and 3.375 (double-s,3H), 1.61 and 1.60 (double-d,3H).

EXAMPLE 7

0.48 g of sodium hydride is placed in 10 ml of absolute dimethylformamide. 1.96 g of o-chloro-p-trifluoromethyl-phenol are added dropwise and the mixture is stirred for 1 hour. 2.6 g of N-(5-fluoro-2-nitrobenzoyl)-S,S-dimethyl-sulphoximine are added and the mixture is heated to 100° C. for 90 minutes. The mixture is then cooled, poured on to 100 ml of ice-water and extracted with 50 ml of ethyl acetate. The ethyl acetate phase is washed with water, dried and evaporated, and the residue is purified by chromatography and crystallized from diethyl ether. There is obtained 1 g of N-[5-(o-chloro-p-trifluoromethyl-phenoxy)-2-nitrobenzoyl]-S,S-dimethyl-sulphoximine, m.p. 122° C.

The N-(5-fluoro-2-nitrobenzoyl)-S,S-dimethyl-sulphoximine used as the starting material can be prepared as follows:

A solution of 26.8 g of 5-fluoro-2-nitrobenzoic acid in 50 ml of thionyl chloride is heated at reflux temperature for 1 hour. The excess thionyl chloride is then distilled off and the residue is dissolved in 50 ml of methylene chloride. A solution of 13.5 g of dimethyl sulphoximine in 11.5 g of pyridine is added dropwise at 0° C. and the mixture is stirred for 1 hour. The mixture is subsequently evaporated and the residue is purified by chromatography on a ten-fold amount of silica gel. The product is crystallized from toluene. There is thus obtained N-(5-fluoro-2-nitrobenzoyl)-S,S-dimethyl-sulphoximine, m.p. 113°–115° C.

EXAMPLE 8

0.14 g of sodium hydride is placed in 20 ml of dimethyl sulphoxide. A solution of 1.55 g of N-(5-hydroxy-2-nitrobenzoyl)-S,S-dimethyl-sulphoximine in 10 ml of dimethyl sulphoxide is added dropwise and the mixture is stirred at 40° C. for 3 hours. 1.0 g of 2-fluoro-5-trifluoromethyl-pyridine is subsequently added to the mixture and the resulting mixture is heated at 70° C. for 16 hours.

For the working-up, the cooled mixture is poured into 100 ml of 2N sodium hydroxide and the aqueous mixture is extracted three times with 50 ml of ethyl acetate each time. The combined organic phases are washed twice with 100 ml of water each time, dried and evaporated, and the residue is purified by chromatogaphy on silica gel with n-hexane/ethyl acetate (9:1).

The thus-obtained product, N-[5-(5-trifluoromethyl-2-pyridyloxy)-2-nitrobenzoyl]-S,S-dimethyl-sulphoximine, has the same physical data as the corresponding compound I in Example 1 (9th end product).

The N-(5-hydroxy-2-nitrobenzoyl)-S,S-dimethyl-sulphoximine used as the starting material can be prepared as follows:

A solution of 20.6 g of dicyclohexylcarbodiimide in 100 ml of methylene chloride is added dropwise at room temperature while stirring during 10 minutes to a suspension of 22.5 g of 5-acetoxy-2-nitrobenzoic acid in 500 ml of methylene chloride. A solution of 9.3 g of dimethyl sulphoximine in 50 ml of methylene chloride is subsequently added dropwise to the mixture during 5 minutes and the resulting mixture is stirred at room temperature for 3 hours. The insoluble dicyclohexylurea formed is filtered off under suction and the filtrate is evaporated under reduced pressure. The residue is purified by chromatography on silica gel with methylene chloride/ethyl acetate (1:1).

There is obtained N-(5-acetoxy-2-nitrobenzoyl)-S,S-dimethyl-sulphoximine as a viscous yellow oil; $^1$H-NMR (CDCl$_3$): 7.94 (d,1H), 7.50 (d,1H), 7.28 (q,1H), 3.40 (s,6H), 2.36 (t,3H).

A solution of 30.0 g of N-(5-acetoxy-2-nitrobenzoyl)-S,S-dimethyl-sulphoximine in 500 ml of methanol is treated with 150 ml of 2N sodium hydroxide and the mixture is stirred at room temperature for 20 minutes. The resulting solution is then adjusted to about pH 4 with 100 ml of 2N hydrochloric acid and the methanol is distilled off under reduced pressure. The residue is saturated with sodium chloride solution and extracted with ethyl acetate, and the organic phase is dried and evaporated. The crystalline residue is then recrystallized from hot ethyl acetate. There is obtained N-(5-hydroxy-2-nitrobenzoyl)-S,S-dimethyl-sulphoximine as yellow crystals, m.p. 146°–149° C.; $^1$H-NMR (CMSO): 7.90 (d,1H), 6.95 (d,1H), 6.90 (q,1H), 3.44 (s,6H).

EXAMPLE 9

400 ml of 94% sulphuric acid are added dropwise during 10 minutes to a solution of 195.9 g of N-[3-(o-chloro-p-trifluoromethyl-phenoxy)-benzoyl]-S,S-dimethyl-sulphoximine in 750 ml of 1,2-dichloroethane. The mixture is cooled to −5° C. while stirring and treated dropwise during 30 minutes with a solution of 50.55 g of potassium nitrate in 400 ml of 94% sulphuric acid. The stirring at −5° C. is continued for a further 15 minutes. The mixture is subsequently poured on to 3.5 kg of ice and the separated oil is extracted three times with 1.5 l of methylene chloride each time. The combined extracts are washed neutral four times with 750 ml of water each time, dried over anhydrous sodium sulphate and evaporated to dryness under reduced pressure. After dissolving the residue in 750 ml of diethyl ether the solution is seeded and treated with 250 ml of n-hexane. The resulting crystals are then filtered off under suction, washed twice with 250 ml of diethyl ether each time and dried, 155.5 g of product being obtained. By evaporating the mother liquor to dryness and purifying the residue (65.0 g) with diethyl ether on a column of 1.25 kg of silica gel 60 there are obtained a further 14.2 g of product in the form of yellow crystals. The total amount of product obtained is thus 169.7 g (77.7% of the theoretical yield) of N-[5-(o-chloro-p-trifluoromethyl-phenoxy)-2-nitrobenzoyl]-S,S-dimethyl-sulphoximine, m.p. 118°–125° C.

The N-[3-(o-chloro-p-trifluoromethyl-phenoxy)-benzoyl]-S,S-dimethyl-sulphoximine used as the starting material can be prepared in accordance with the five-step process described hereinafter:

(a) A solution of 56.11 g of potassium tert.butylate in 400 ml of absolute tetrahydrofuran is added dropwise during 10 minutes while stirring to a solution of 46.57 g of dimethyl sulphoximine in 900 ml of absolute tetrahydrofuran, the temperature of the mixture rising to 35° C. After completion of the addition the mixture is stirred for 1 hour. The dimethyl sulphoximine potassium salt is thus formed in suspension.

(b) A solution of 99.3 g of m-acetoxybenzoyl chloride in 150 ml of absolute tetrahydrofuran is added dropwise at −35° C. during 20 minutes while stirring to the dimethyl sulphoximine potassium salt suspension and the mixture is then stirred at −35° C. for 30 minutes. N-(m-Acetoxybenzoyl)-S,S-dimethyl-sulphoximine is thus formed in suspension.

(c) The cooling bath is removed, the yellow suspension is treated with a solution of 40.0 g of sodium hydroxide in 200 ml of water and the mixture is stirred at room temperature for 1.5 hours. The two-phase system is thereafter extracted three times with 150 ml of ethyl acetate each time, the organic phase is separated and this is extracted with 150 ml of 2N sodium hydroxide. The combined aqueous phases are acidified to about pH 2 with 32% hydrochloric acid, saturated with sodium chloride and subsequently extracted four times with 700 ml of ethyl acetate each time.

The combined organic extracts are dried over anhydrous sodium sulphate and evaporated to dryness under reduced pressure. The resulting solid residue is then dissolved in 1 l of ethyl acetate at 80° C., the solution is concentrated to about 0.5 l by heating and the residue is cooled to room temperature. The resulting crystals are filtered off under suction, rinsed with 200 ml of n-hexane and dried. There are obtained 91.91 g (86.2% of the theoretical yield) of N-(m-hydroxybenzoyl)-S,S-dimethyl-sulphoximine, m.p. 148°–150° C.

(d) 21.81 g of sodium hydride (55% dispersion in oil) are placed in 1.6 l of absolute dimethyl sulphoxide and subsequently a solution of 106.63 g of N-(m-hydroxybenzoyl)-S,S-dimethyl-sulphoximine in 550 ml of absolute dimethyl sulphoxide is added dropwise during 15 minutes while stirring. The sodium salt of N-(m-hydroxybenzoyl)-S,S-dimethyl-sulphoximine is thus prepared in situ.

(e) 0.15 g of copper powder (prepared electrolytically) is added to the mixture obtained according to paragraph (d) and the resulting mixture is heated to 150° C. A solution of 107.51 g of 1,2-dichloro-4-trifluoromethylbenzene in 300 ml of dimethyl sulphoxide is subsequently added dropwise during 30 minutes while stirring well and the mixture is stirred for 45 minutes at 150° C. and at pH 8–9. The solvent is thereafter distilled off to a large extent under reduced pressure, the residue is taken up in 1 l of methylene chloride and the insoluble constituents are removed by filtration. The filtrate is washed successively twice with 250 ml of water each time, with 600 ml of 0.5N sodium hydroxide and twice with 250 ml of water each time, dried over anhydrous sodium sulphate and evaporated to dryness. The oily residue is subsequently dissolved in 600 ml of diethyl ether and the solution is treated with 500 ml of n-hexane and seeded. The resulting crystals are filtered off under suction, washed twice with 100 ml of diethyl ether each time and dried, there being obtained 99.63 g of product. By evaporating the mother liquor to dryness and purifying the residue (54.0 g) with ethyl acetate/n-hexane (2:1) on a column of 1.4 kg of silica gel there are obtained a further 32.13 g of crystals. The crystalline product (total 131.76 g) is purified further by dissolving the crystals in 1.4 l of methylene chloride, treating the solution with carbon and concentrating to a large extent. The residue is then taken up in 250 ml of diethyl ether and the solution is treated with 150 ml of n-hexane and seeded. The resulting crystals are finely filtered off under suction, washed with 100 ml of diethyl ether each time and dried. There are obtained 109.1 g (55.7% of the theoretical yield) of N-[3-(o-chloro-p-trifluoromethyl-phenoxy)-benzoyl]-S,S-dimethyl-sulphoximine, m.p. 110°–113° C.

II. Formulation Examples

EXAMPLE 10

| Emulsifiable concentrate | |
|---|---|
| Active substance of formula I | 250 g |
| Castor oil-(20)-ethoxylate | 50 g |
| Calcium dodecylbenzene sulphonate | 25 g |
| Mixture of o-, m- and p-xylenes | 150 g |
| N—Methyl-2-pyrrolidone | to 1000 ml |

The active substance, the castor oil-(20)-ethoxylate (non-ionic emulsifier) and the calcium dodecylbenzene sulphonate (anionic emulsifier) are dissolved in the xylene mixture (auxilliary solvent) and in a portion of the N-methyl-2-pyrrolidone (main solvent) and the solution is subsequently made up to a volume of 1000 ml with a further amount of N-methyl-2-pyrrolidone.

The thus-obtained emulsifiable concentrate can be diluted with water to give an emulsion which is stable for hours. Such an emulsion is suitable as a ready-for-use spray liquor.

EXAMPLE 11

For the manufacture of an emulsifiable concentrate (1,2,3,4 or 5) the ingredients listed hereinafter are mixed with one another:

| Emulsifiable concentrate 1 | |
|---|---|
| Active substance of formula I | 250 g |
| N—Methyl-2-pyrrolidone | 300 g |
| Emulsifier A[1] | 100 g |
| Emulsifier B[2] | 25 g |
| Solvent mixture of alkylbenzenes | to 1000 ml |
| Emulsifiable concentrate 2 | |
| Active substance of formula I | 250 g |
| Dimethylformamide | 300 g |
| Fatty alcohol-(10)-ethoxylate | 75 g |
| Calcium dodecylbenzene sulphonate | 25 g |
| Solvent mixture of alkylbenzenes | to 1000 ml |
| Emulsifiable concentrate 3 | |
| Active substance of formula I | 500 g |
| Castor oil-(30)-ethoxylate | 50 g |
| Calcium dodecylbenzene sulphonate | 25 g |
| Cyclohexanone | ad 1000 ml |
| Emulsifiable concentrate 4 | |
| Active substance of formula I | 750 g |
| Alkylbenzene-(8)-ethoxylate | 50 g |
| Ammonium alkylbenzene sulphonate | 25 g |
| Solvent mixture of xylenes | to 1000 ml |
| Emulsifiable concentrate 5 | |
| Active substance of formula I | 250 g |
| Castor oil-(20)-ethoxylate | 50 g |
| Calcium dodecylbenzene sulphonate | 25 g |
| Cyclohexanone | 200 g |
| Solvent mixture of alkylbenzenes | to 1000 ml |

[1]Emulsifier consisting of 60 parts of an ethylene oxide-propylene oxide block polymerizate, 20 parts of calcium dodecylbenzene sulphonate and 20 parts of isobutanol/$C_{10}$-alkylbenzenes mixture.
[2]Emulsifier consisting of 70 parts of calcium dodecylbenzene sulphonate and 30 parts of isobutanol/$C_{10}$-alkylbenzenes mixture.

The thus-obtained concentrate (1,2,3,4 or 5) emulsifies spontaneously in water and the resulting emulsion is suitable as a ready-for-use spray liquor.

EXAMPLE 12

For the manufacture of a spray powder (1 or 2) the ingredients listed hereinafter are mixed with one another and the mixture is finely ground:

| | Weight percent |
|---|---|
| Spray powder 1 | |
| Active substance of formula I | 50 |
| Hydrated silicic acid | 5 |
| Sodium lauryl sulphate | 1 |
| Sodium lignosulphonate | 2 |
| Kaolin | 42 |
| Spray powder 2 | |
| Active substance of formula I | 25 |
| Hydrated silicic acid | 30 |
| Alkylphenol-(12)-ethoxylate | 4 |
| Polycarboxylic acid sodium salt | 4 |
| Kaolin | 37 |

The thus-obtained powder (1 or 2) can be wetted with water. The resulting suspension is suitable as a ready-for-use spray liquor.

EXAMPLE 13

For the manufacture of a dusting composition the ingredients listed hereinafter are mixed with one another and the mixture is finely ground:

| | Weight percent |
|---|---|
| Active substance of formula I | 10 |
| Hydrated silicic acid | 7.5 |
| Talc | 82.5 |

EXAMPLE 14

For the manufacture of a granulate the ingredients listed hereinafter are mixed with one another:

| | Weight percent |
|---|---|
| Active substance of formula I | 5 |
| Dipropylene glycol | 5 |
| Pumice stone granulate | 90 |

We claim:

1. A compound of the formula

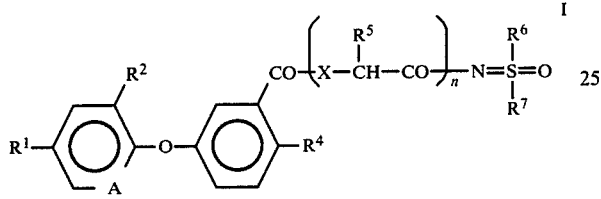

wherein A is N or CR$^3$,

R$^1$ is halogen or trifluoromethyl,

R$^2$ and R$^3$ independently of one another are hydrogen or halogen,

R$^4$ is halogen, nitro,

R$^5$ is hydrogen or methyl,

R$^6$ is C$_{1-6}$-alkyl and

R$^7$ is C$_{1-6}$-alkyl, phenyl, or phenyl substituted with halogen, C$_{1-4}$-alkyl, C$_{1-4}$-alkoxy and/or nitro, n is 0, X is oxygen.

2. The compound according to claim 1, wherein R$^6$ is C$_{1-6}$-alkyl and R$^7$ is C$_{1-6}$-alkyl, phenyl, or phenyl substituted with halogen, C$_{1-4}$-alkyl, C$_{1-4}$-alkoxy and/or nitro.

3. The compound according to claim 1, wherein A is CR$^3$, R$^1$ is trifluoromethyl, R$^2$ is chlorine and R$^3$ is hydrogen.

4. The compound according to claim 3, wherein R$^4$ is nitro.

5. The compound according to claim 4, wherein X is oxygen.

6. N-[5-(o-Chloro-p-trifluoromethyl-phenoxy)-2-nitro-benzoyl]-S,S-dimethyl-sulphoximine.

7. A compound according to claim 1 selected from the group consisting of:
N-[5-(o-Chloro-p-trifluoromethyl-phenoxy)-2-nitrobenzoyl]-S-ethyl-S-methyl-sulphoximine,
N-[5-(o-chloro-p-trifluoromethyl-phenoxy)-2-nitrobenzoyl]-S,S-diethyl-sulphoximine,
N-[5-(o-chloro-p-trifluoromethyl-phenoxy)-2-nitrobenzoyl]-S-methyl-S-phenyl-sulphoximine,
N-[5-(o-chloro-p-trifluoromethyl-phenoxy)-2-nitrobenzoyl]-S-(n-hexyl)-S-methyl-sulphoximine,
N-{2-[5-(o-chloro-p-trifluoromethyl-phenoxy)-2-nitro-benzoyloxy]-propionyl}-S-methyl-S-phenyl-sulphoximine and
N-{2-[5-(o-chloro-p-trifluoromethyl-phenoxy)-2-nitro-benzoyloxy]-propionyl}-S-ethyl-S-methyl-sulphoximine.

8. A compound according to claim 1 selected from the group consisting of:
N-[5-(o-Chloro-p-trifluoromethyl-phenoxy)-2-nitro-benzoyl]-S-methyl-S-(p-chlorophenyl)-sulphoximine,
N-[5-(o-chloro-p-trifluoromethyl-phenoxy)-2-nitrobenzoyl]-S-methyl-S-(p-tolyl)-sulphoximine,
N-[5-(o-chloro-p-trifluoromethyl-phenoxy)-2-nitrobenzoyl]-S-methyl-S-(o-chlorophenyl)-sulphoximine,
N-[5-(5-trifluoromethyl-2-pyridyloxy)-2-nitrobenzoyl]-S,S-dimethyl-sulphoximine
N-[5-(3,5-dichloro-2-pyridyloxy)-2-nitrobenzoyl]-S,S-dimethyl-sulphoximine,
N-[5-(3-chloro-5-trifluoromethyl-2-pyridyloxy)-2-nitro-benzoyl]-S,S-dimethyl-sulphoximine,
N-[2-chloro-5-(o-chloro-p-trifluoromethyl-phenoxy)-benzoyl]-S,S-dimethyl-sulphoximine,
N-[5-(o-chloro-p-trifluoromethyl-phenoxy)-2-iodobenzoyl]-S,S-dimethyl-sulphoximine,
N-[5-(o-chloro-p-trifluoromethyl-phenoxy)-2-nitrobenzoyl]-S,S-tetramethylene-sulphoximine,
N-[5-(o-chloro-p-trifluoromethyl-phenoxy)-2-nitrobenzoyl]-S-methyl-S-(p-nitrophenyl)-sulphoximine,
N-[5-(o-chloro-p-trifluoromethyl-phenoxy)-2-nitrobenzoyl]-S-methyl-S-(p-methoxyphenyl)-sulphoximine,
N-{2-[5-(o-chloro-p-trifluoromethyl-phenoxy)-2-nitro-benzoyloxy]-propionyl}-S-methyl-S-(p-chlorophenyl)-sulphoximine,
N-{2-[5-(o-chloro-p-trifluoromethyl-phenoxy-2-nitro-benzoyloxy]-propionyl}-S-methyl-S-(p-tolyl)-sulphoximine,
N-{2-[5-(o-chloro-p-trifluoromethyl-phenoxy)-2-nitro-benzoyloxy]-propionyl}-S,S-tetramethylene-sulphoximine,
N-{[5-(o-chloro-p-trifluoromethyl-phenoxy)-2-nitro-benzoyloxy]-acetyl}-S,S-dimethyl-sulphoximine,
N-{2-[5-(o-chloro-p-trifluoromethyl-phenoxy)-2-nitro-benzoyloxy]-propionyl}-S,S-dimethyl-sulphoximine,
N-{2-[5-(o-chloro-p-trifluoromethyl-phenoxy)-2-nitro-benzoyloxy]-propionyl}-S-methyl-S-(p-methoxyphenyl)-sulphoximine and
N-{2-[5-(o-chloro-p-trifluoromethyl-phenoxy)-2-nitro-benzoyloxy]propionyl}-S-methyl-S-(p-nitrophenyl)-sulphoximine.

9. A herbicidal composition which comprises an inert carrier material and, as the active ingredient, an amount of a compound of claim 1 which is effective as a herbicide.

10. The herbicidal composition of claim 9, wherein the active ingredient is an effective amount of N-[5-(o-chloro-p-trifluoromethyl-phenoxy)-2-nitrobenzoyl]-S,S-dimethyl-sulphoximine.

11. A herbicidal composition which comprises an inert carrier material and, as the active ingredient, an amount of a compound of claim 7 which is effective as a herbicide.

12. A herbicidal composition which comprises an inert carrier material and, as the active ingredient, an amount of a compound of claim 8 which is effective as a herbicide.

13. The method for combatting weeds which comprises applying to the locus to be protected, a herbicidally effective amount of the compound of claim 1.

14. The method for combatting weeds which comprises applying to the locus to be protected, a herbicidally effective amount of a compound of claim 6.

15. The method for combating weeds which comprises applying to the locus to be protected, a herbicidally effective amount of a compound of claim 7.

16. The method for combatting weeds which comprises applying to the locus to be protected, a herbicidally effective amount of a compound of claim 8.

17. A method for combatting weeds which comprises applying to the locus to be protected, a herbicidally effective amount of a composition of claim 9.

18. A method for combatting weeds which comprises applying to the locus to be protected, a herbicidally effective amount of the composition of claim 10.

19. N-(5-Fluoro-2-nitrobenzoyl)-S,S-dimethyl-sulphoximine.

20. N-(5-Hydroxy-2-nitrobenzoyl)-S,S-dimethyl-sulphoximine.

21. N-[3-(o-Chloro-p-trifluoromethyl-phenoxy)-benzoyl]-S,S-dimethyl-sulphoximine.

* * * * *